United States Patent
Heston et al.

(10) Patent No.: US 6,897,062 B1
(45) Date of Patent: May 24, 2005

(54) DNA ENCODING THE PROSTATE-SPECIFIC MEMBRANE ANTIGEN-LIKE GENE AND USES THEREOF

(75) Inventors: Warren Heston, Chagrin Falls, OH (US); Denise O'Keefe, Sagamore Hills, OH (US)

(73) Assignee: Sloan-Kettering Institute for Cancer Research, New York, NY (US)

(*) Notice: Subject to any disclaimer, the term of this patent is extended or adjusted under 35 U.S.C. 154(b) by 4 days.

(21) Appl. No.: 09/973,382

(22) Filed: Oct. 9, 2001

Related U.S. Application Data

(63) Continuation-in-part of application No. PCT/US00/09417, filed on Apr. 7, 2000.
(60) Provisional application No. 60/128,839, filed on Apr. 9, 1999.

(51) Int. Cl.[7] ............................................. C12N 15/85
(52) U.S. Cl. ................. 435/325; 435/252.3; 435/320.1; 435/348; 435/410; 536/23.1; 536/23.5; 530/350
(58) Field of Search ............................. 435/69.1, 320.1, 435/252.3, 325; 536/23.1, 23.5; 530/350, 300

(56) References Cited

U.S. PATENT DOCUMENTS 5,962,237 A * 10/1999 Ts'o .......................... 435/9.23
6,387,888 B1 * 5/2002 Mincheff et al. ............. 514/44

OTHER PUBLICATIONS

Bowie et al (Science, 1990, 257 : 1306–1310).*
Burgess et al, (Journal of Cell Biology, 1990, 11:2129–2138).*
Lazar et al. Molecular and Cell Biology, 1988, 8: 1247–1252.*
Miller (1995, FASEB J., vol. 9, pp. 190–199).*
Deonarain (1998, Expert Opin. Ther. Pat., vol. 8, pp. 53–69.*
Verma (Sep. 1997, Nature, vol. 389, pp. 239–242).*
Crystal (1995, Science, vol. 270, pp, 404–410).*
Su SL et al, 1995, Cancer Res, 55: 1441–1443.*
MPSRCH search report, 2004, us–09–973–382c–1.oli.mi, p.7.*

* cited by examiner

*Primary Examiner*—Susan Ungar
*Assistant Examiner*—Minh-Tam Davis
(74) *Attorney, Agent, or Firm*—Benjamin Aaron Adler

(57) ABSTRACT

The present invention discloses a new gene, termed PSMA-like, that is very similar to the prostate-specific membrane antigen (PSMA) gene and cross-reacts with current detection methods for PSMA. The present invention also provides for a method of distinguishing the PSMA and PSMA-like mRNAs and/or proteins for diagnostic and therapeutic strategies that desire specific targeting of either the PSMA or PSMA-like gene.

5 Claims, 6 Drawing Sheets

```
PSMA        1  MWNLLHETDSAVATARRPRWLCAGALVLAGGFFLLGFLFG  40
PSMA-Like   1                                              0

PSMA       41  WFIKSSNEATNITPKHNMKAFLDELKAENIKKFLYNFTQI  80
PSMA-Like   1                                              0

PSMA       81  PHLAGTEQNFQLAKQIQSQWKEFGLDSVELAHYDVLLSYP 120
PSMA-Like   1                                              0

PSMA      121  NKTHPNYISIINEDGNEIFNTSLFEPPPPGYENVSDIVPP 160
PSMA-Like   1                                              0

PSMA      161  FSAFSPQGMPEGDLVYVNYARTEDFFKLERDMKINCSGKI 200
PSMA-Like   1                                              0

PSMA      201  VIARYGKVFRGNKVKNAQLAGAKGVILYSDPADYFAPGVK 240
PSMA-Like   1                                              0

PSMA      241  SYPDGWNLPGGGVQRGNILNLNGAGDPLTPGYPANEYAYR 280
PSMA-Like   1                                              0

PSMA      281  RGIAEAVGLPSIPVHPIGYYDAQKLLEKMGGSAPPDSSWR 320
PSMA-Like   1                             MGGSAPPDSSWR  12
                                           ***********

PSMA      321  GSLKVPYNVGPGFTGNFSTQKVKMHIHSTNEVTRIYNVIG 360
PSMA-Like  13  GSLKVSYNVGPGFTGNFSTQKVKMHIHSTNEVTRIYNVIG  52
               ***** **********************************

PSMA      361  TLRGAVEPDRYVILGGHRDSWVFGGIDPQSGAAVVHEIVR 400
PSMA-Like  53  TLRGAVEPDRYVILGGHRDSWVFGGIDPQSGAAVVHETVR  92
               ************************************ **

PSMA      401  SFGTLKKEGWRPRRTILFASWDAEEFGLLGSTEWAEENSR 440
PSMA-Like  93  SFGTLKKEGWRPRRTILFASWDAEEFGLLGSTEWAEDNSR 132
               ************************************ ***
```

Fig. 4A

```
PSMA      441 LLQERGVAYINADSSIEGNYTLRVDCTPLMYSLVHNLTKE 480
PSMA-Like 133 LLQERGVAYINADSSIEGNYTLRVDCTPLMYSLVYNLTKE 172
              *************************************  ****

PSMA      481 LKSPDEGFEGKSLYESWTKKSPSPEFSGMPRISKLGSGND 520
PSMA-Like 173 LKSPDEGFEGKSLYESWTKKSPSPEFSGMPRISKLGSGND 212
              ****************************************

PSMA      521 FEVFFQRLGIASGRARYTKNWETNKFSGYPLYHSVYETYE 560
PSMA-Like 213 FEVFFQRLGIASGRARYTKNWETNKFSGYPLYHSVYETYE 252
              ****************************************

PSMA      561 LVEKFYDPMFKYHLTVAQVRGGMVFELANSIVLPFDCRDY 600
PSMA-Like 253 LVEKFYDPMFKYHLTVAQVRGGMVFELANSIVLPFDCRDY 292
              ****************************************

PSMA      601 AVVLRKYADKIYSISMKHPQEMKTYSVSFDSLFSAVKNFT 640
PSMA-Like 293 AVVLRKYADKIYNISMKHPQEMKTYSLSFDSLFSAVKNFT 332
              ************ ************* *************

PSMA      641 EIASKFSERLQDFDKSNPIVLRMMNDQLMFLERAFIDPLG 680
PSMA-Like 333 EIASKFSERLQDFDKSNPILLRMMNDQLMFLERAFIDPLG 372
              ******************* ********************

PSMA      681 LPDRPFYRHVIYAPSSHNKYAGESFPGIYDALFDIESKVD 720
PSMA-Like 373 LPDRPFYRHVIYAPSSHNKYAGESFPGIYDALFDIESKVD 412
              ****************************************

PSMA      721 PSKAWGEVKRQIYVAAFTVQAAAETLSEVA (SEQ ID NO: 4)
PSMA-Like 413 PSKAWGDVKRQISVAAFTVQAAAETLSEVA (SEQ ID NO: 2)
              ****** ***** *****************
```

Fig. 4B

Fig. 6

DNA ENCODING THE PROSTATE-SPECIFIC MEMBRANE ANTIGEN-LIKE GENE AND USES THEREOF

CROSS-REFERENCE TO RELATED APPLICATION

This patent application is a continuation-in-part of the international application PCT/US00/9417, filed Apr. 7, 2000, which claims benefit of provisional patent application U.S. Ser. No. 60/128,839, filed Apr. 9, 1999, now abandoned.

FEDERAL FUNDING LEGEND

This invention was produced in part using funds obtained through grant DK/CA47650 from NIDDK/NCI. Consequently, the federal government has certain rights in this invention.

BACKGROUND OF THE INVENTION

1. Field of the Invention

The present invention relates generally to the field of cell biology. More specifically, the present invention relates to the prostate-specific membrane antigen-like gene and uses thereof.

2. Description of the Related Art

Prostate cancer is the leading cause of cancer and second leading cause of cancer death among American males. Although prostate tumors in the initial stages are slow growing and can be treated by radical prostatectomy and hormone deprivation, once the tumor is hormone refractory and/or has metastasized, there are few options for the patient. The major current biomarker for this disease is prostate specific antigen (PSA), however PSA is of limited value for assessing patients with disseminated disease as it is down-regulated under conditions of low androgens, and these patients undergo androgen-ablative therapy. More markers for prostate cancer are needed that have increased effectiveness over those currently used for clinical diagnosis and patient management, as well as for future therapeutic targets of this disease.

Prostate specific membrane antigen (PSMA) is an ideal potential target for use in determining patient management, and therapeutic strategies against prostate cancer. The prostate specific membrane antigen is highly expressed in virtually 100% of prostate cancers and, in contrast to PSA, the prostate specific membrane antigen is further upregulated under conditions of androgen deprivation. Furthermore, in the normal prostate, alternative splicing of prostate specific membrane antigen mRNA produces a truncated form of the protein (which has been designated PSM') that is missing the intracellular and transmembrane domains, and as such, this form is localized to the cytosol [5]. At some stage during tumor initiation or progression, there is a change in the mRNA splicing that leads to the majority of prostate specific membrane antigen transcripts comprising the transmembrane domain, thereby producing a 750 amino acid membrane-bound protein (unlike PSA, which is secreted into the circulatory system), the majority of which is located extracellularly and is readily available for therapeutic targeting, clinical imaging or other diagnostic-type assays [5]. Prostate specific membrane antigen is already used clinically as the target of the imaging agent ProstaScint, and is the focus of a number of therapeutic strategies in development.

The known functions of the prostate specific membrane antigen carboxypeptidase are as an NAALadase and folate hydrolase. Expression of prostate specific membrane antigen is largely confined to the prostate gland, although expression can also be detected in the duodenum brain, salivary gland, kidney, and colon [2,6]. In prostate cancer, enhanced expression of prostate specific membrane antigen correlates with increasing grade of tumor [7].

Additionally, it now seems that therapeutic targeting of the prostate specific membrane antigen molecule may have additional advantages, since prostate specific membrane antigen expression has been found in the endothelial cells of tumor neovasculature of almost all types of tumors examined to date, including bladder, renal, breast and lung carcinomas [1,6]. No prostate specific membrane antigen expression has been found in any kind of normal established non-neovasculature. As such, a therapeutic approach targeted at prostate specific membrane antigen could have broad implications for the treatment of many types of solid tumors, and several groups are now attempting to utilize prostate specific membrane antigen as a treatment target.

However, although prostate specific membrane antigen is very highly expressed in normal prostate (PSM'; the cytosolic form) and in cancer of the prostate (PSMA; the membrane bound form), there are other tissues in the body that express low levels of prostate specific membrane antigen or a similar mRNA, including kidney, proximal small intestine and brain [4]. This mRNA could either be due to expression of the prostate specific membrane antigen gene, or another related gene such as the PSMA-like gene. Furthermore, one of the major enzymes involved in neurotransmission in the brain is NAALADase, which has the same enzymatic characteristics as prostate specific membrane antigen [7]. Accordingly, it is important to be able to distinguish between prostate- or cancer-derived prostate specific membrane antigen and PSMA-like mRNA from other tissues if prostate specific membrane antigen is going to be used as a clinical marker via techniques like RT-PCR or for therapeutic strategies, which, for example, may use antibodies.

Fluorescent in situ hybridization (FISH) mapping using prostate specific membrane antigen cDNA as a probe indicates that there may be two very similar genes both residing on chromosome 11 [8]. Both genes have been mapped against a human-hamster radiation hybrid panel and determined that one of the genes resides on chromosome 11p11.2, while the other gene resides on chromosome 11q14.3 [9]. It was recently determined that the gene on chromosome 11p11.2 is the PSMA gene originally cloned from the prostatic cancer cell line LNCaP [9], while a highly conserved duplication of the PSMA gene, including at least some intronic sequences, is located on chromosome 11q, a region which is known to have been duplicated to chromosome 11p an estimated 22 million years ago [16,17]. Therefore, the so-called non-prostatic expression of the prostate specific membrane antigen gene is due to expression of another highly similar, but distinct gene, herein designated the PSMA-like gene, arising from the aforementioned gene duplication. Tumor targeting for therapeutic approaches or clinical assays relies on the specificity of the marker targeted. As the prostate specific membrane antigen and PSMA-like genes have a common ancestral gene and only diverged from each other 22 million years ago [9], it is likely that the two genes are extremely similar to each other both in sequence and in function.

The prior art is deficient in means of distinguishing between the prostate specific membrane antigen gene and the PSMA-like gene, and their respective protein products. The present invention fulfills this long-standing need and desire in the art.

SUMMARY OF THE INVENTION

Prostate specific membrane antigen is a 100 kD type II transmembrane protein with folate hydrolase and NAALADase activity. Prostate specific membrane antigen is highly expressed in prostate cancer and the vasculature of most solid tumors, and is currently the target of a number of diagnostic and therapeutic strategies. PSMA is also expressed in the brain, and is involved in conversion of the major neurotransmitter, NAAG (n-acetyl-aspartyl glutamate) to NAA and free glutamate, the levels of which are disrupted in several neurological disorders including multiple sclerosis, amyotrophic lateral sclerosis, Alzheimer's disease and schizophrenia.

The prostate specific membrane antigen gene (having the nucleotide sequence shown in SEQ ID No. 3) encoding prostate specific membrane antigen was recently mapped to 11p11.2, and a gene homologous (PSMA-like), but not identical, to prostate specific membrane antigen was mapped to chromosome 11q14.3, which was subsequently mapped to the schizophrenia disorder type II locus. The mRNA tissue distribution pattern of the prostate specific membrane antigen gene and PSMA-like gene was examined using assays that specifically distinguish between the two genes by exploiting single base coding differences. Results indicate that the PSMA-like gene is expressed, as determined by RT-PCR, RNase protection assay, or using specific primers, and has a tissue distribution differing from that of the PSMA gene.

The present invention characterizes the differences between the prostatic and non-prostatic forms of prostate specific membrane antigen at the nucleic acid level, the protein level and functional level. The ability to distinguish between the PSMA and PSMA-like genes is essential for the utility of prostate specific membrane antigen, both as a prostate cancer marker and as a therapeutic target.

In one embodiment of the present invention, there is provided an isolated DNA fragment encoding a mammalian PSMA-like protein selected from the group consisting of (a) an isolated DNA fragment which encodes a PSMA-like protein; (b) an isolated DNA fragment which hybridizes to the isolated DNA fragment of (a) and which encodes a PSMA-like protein; and (c) an isolated DNA fragment differing from the isolated DNA fragments of (a) and (b) in codon sequence due to the degeneracy of the genetic code, and which encodes a PSMA-like protein; Preferably, the DNA fragment has the sequence shown in SEQ ID No. 1 or fragments thereof, and the PSMA-like protein has the amino acid sequence shown in SEQ ID No. 2 or fragment thereof.

In another embodiment of the present invention, there is provided an isolated and purified PSMA-like protein coded for by DNA selected from the group consisting of (a) isolated DNA which encodes a PSMA-like protein; (b) isolated DNA which hybridizes to the isolated DNA of (a) and which encodes a PSMA-like protein; and (c) isolated DNA differing from the isolated DNAs from (a) and (b) in codon sequence due to the degeneracy of the genetic code, and which encodes a PSMA-like protein. Preferably, the PSMA-like protein has an amino acid sequence shown in SEQ ID No. 2 or fragments thereof.

In still another embodiment of the present invention, there is provided a method of distinguishing PSMA gene expression from PSMA-like gene expression, comprising the steps of: (a) contacting a sample with one or more oligonucleotide primer(s) under hybridizing conditions, wherein the sample comprises RNA; (b) performing RT-PCR on the sample, thereby producing RT-PCR products; (c) contacting the RT-PCR products with an appropriate restriction enzyme, thereby producing digested RT-PCR products; and (d) analyzing the digested RT-PCR products, wherein prostate specific membrane antigen gene expression is distinguished from PSMA-like gene expression by detection of fragment size(s) in the digested RT-PCR products, wherein digested PSMA-specific RT-PCR products comprise different predicted fragment size(s) compared with digested PSMA-like-specific RT-PCR products. Preferably, the oligonucleotide primer is selected from the group consisting of SEQ ID Nos. 5–38.

In yet another embodiment of the present invention, there is provided a method of distinguishing prostate specific membrane antigen protein from PSMA-like protein in a sample, comprising the steps of: (a) contacting the sample with at least one antibody specific for a PSMA protein and/or, at least one antibody specific for a PSMA-like protein under appropriate conditions; and (b) detecting binding of the antibody or antibodies. The specificity of binding is indicative of the presence of PSMA and/or PSMA-like proteins in the sample.

In yet another embodiment of the present invention, there is provided a vector for targeted gene therapy, comprising: a promoter/enhancer region from a PSMA gene or a PSMA-like gene; and a therapeutic gene. PSMA gene promoter/enhancer targets the therapeutic gene to prostate tissues and tumor neovasculature of solid tumors; whereas PSMA-like gene promoter/enhancer targets to non-prostate tissues.

In still yet another embodiment of the present invention, there is provided a method of screening for prostate specific membrane antigen or PSMA-like ligands, comprising the steps of contacting a prostate specific membrane antigen or PSMA-like protein, or fragment thereof, with potential ligands under conditions that permit protein—protein binding; removing non-specific protein—protein binding; and eluting protein bound to the PSMA or PSMA-like protein. Typically, the eluted protein is a ligand for the PSMA or PSMA-like protein.

Also provided in another embodiment of the present invention is a method of imaging cells expressing a prostate specific membrane antigen or PSMA-like protein, comprising the steps of: administering to the cells at least one compound, wherein the compound is specifically directed towards a prostate specific membrane antigen or PSMA-like protein and labeled with a n imaging agent; and detecting the imaging agent in the cells.

Further provided in an embodiment of the present invention is a cytotoxic composition, comprising: a compound specific for either a prostate specific membrane antigen protein or fragment thereof, or a PSMA-like protein or fragment thereof; and a cytotoxic agent.

Further provided is a pharmaceutical composition comprising an antibody directed against a prostate specific membrane antigen protein and does not recognize a PSMA-like protein. Such a composition can be used for diagnosing a cancer or a neurological disorder such as schizophrenia in an individual.

Further provided is a method of inducing cell death in a cell by transfecting said cell with a vector expressing PSMA-like protein. The cell preferably is a prostrate cancer cell such as PC3 prostrate cells.

Also provided are methods for inhibiting cell death such as inhibiting PSMA-like gene expression in a cell or administering an inhibitor of PSMA-like protein to a cell. Other and further aspects, features, and advantages of the present invention will be apparent from the following description of the presently preferred embodiments of the invention. These embodiments are given for the purpose of disclosure.

BRIEF DESCRIPTION OF THE DRAWINGS

The appended drawings have been included herein so that the above-recited features, advantages and objects of the invention will become clear and can be understood in detail. These drawings form a part of the specification. It is to be noted, however, that the appended drawings illustrate preferred embodiments of the invention and should not be considered to limit the scope of the invention.

FIG. 1A shows PCR amplification of the PSMA promoter region reported by [9]. FIG. 1B shows amplification using primers to exon 16 of the PSMA gene. FIG. 1C shows amplification using primers to intron 6 of the PSMA gene. Genomic is normal human DNA, the subsequent 3 lanes used human-hamster hybrid DNA containing the indicated chromosomes. Hamster refers to the parental DNA. Panels A–C clearly show exonic and intronic duplication of the PSMA gene on 11p and 11q, but only 11p contains the prostate specific membrane antigen promoter region.

FIGS. 4A and 4B show the alignment between prostate specific membrane antigen protein (SEQ ID No. 4) and PSMA-like protein (SEQ ID No. 2).

FIG. 6 shows representative, randomly selected microscopic fields of PC3 prostrate cancer cells transfected with various vector constructs. Vectors include those expressing no protein (PC3-neo), PSMA (PC3-PSMA), PSMA/PSMA-like hybrid protein (PC3-PSMA/Like Hybrid), and PSMA-like protein (PC3-PSM Like).

DETAILED DESCRIPTION OF THE INVENTION

Figure 1A:
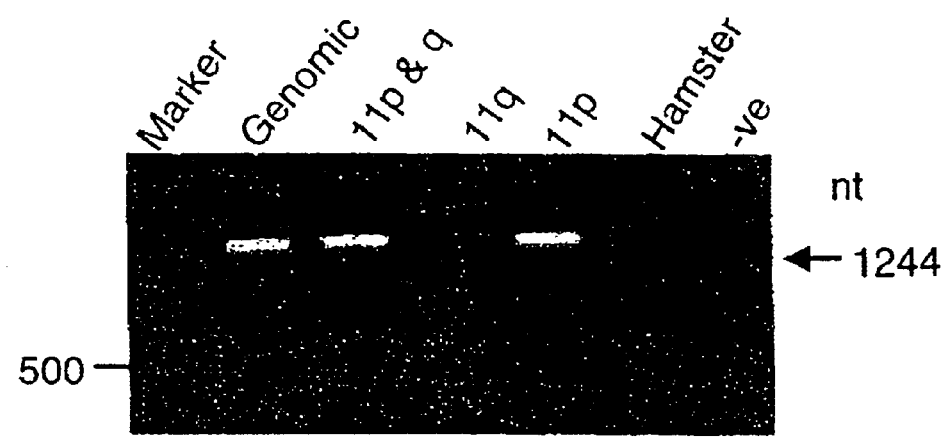
FIGS. 1A-1C show mapping of the prostate specific membrane antigen gene to chromosome 11p.

Prostate specific membrane antigen is expressed on the cell surface making it a useful target for both clinical and therapeutic strategies. While prostate specific membrane antigen appears to be an ideal prostate cancer marker and potential therapeutic target, there have been reports of prostate specific membrane antigen expression in non-prostatic tissues, including brain, kidney and proximal small intestine. Such expression of prostate specific membrane antigen could weaken the potential of this gene as a prostate cancer marker, or at least, produce confusing and conflicting data. However, there is reason to believe that the so-called non-prostatic expression of the prostate specific membrane antigen gene is, in fact, due to expression of a highly similar, but distinct, gene, which is designated as "PSMA-like" gene. The prostate specific membrane antigen gene has recently been mapped to human chromosome 11p11.2, and the "PSMA-like" gene to chromosome 11q14.3. Characterization of the differences between the prostatic and non-prostatic forms of prostate specific membrane antigen at the nucleic acid level, the protein level and functional level is essential for the future utility of prostate specific membrane antigen, both as a prostate cancer marker and as a therapeutic target.

The differences unique to prostate specific membrane antigen can be used to generate specific antibodies for clinical imaging or immunotherapeutic approaches, RT-PCR analysis of bodily fluids specifically for prostate- or prostate cancer-derived cells. It is also possible that the two proteins differ in their enzymatic activity in such a way that prodrugs could specifically target PSMA-expressing tissues. The present invention also provides for analysis of the sequences in the prostate specific membrane antigen gene responsible for expression in the prostate and in prostate cancer. Comparison of the promoter and enhancer sequences from the prostate specific membrane antigen gene with the corresponding regions in the PSMA-like gene (which is not expressed in the prostate) allows elucidation of those sequences responsible for prostate-specific expression. These sequences can be used to generate tissue-specific constructs for use in gene therapy against prostate cancer.

In one embodiment of the present invention, there is provided an isolated DNA fragment encoding a mammalian PSMA-like protein selected from the group consisting of (a) an isolated DNA fragment which encodes a PSMA-like protein; (b) an isolated DNA fragment which hybridizes to the isolated DNA fragment of (a) and which encodes a PSMA-like protein; and (c) an isolated DNA fragment differing from the isolated DNA fragments of (a) and (b) in codon sequence due to the degeneracy of the genetic code, and which encodes a PSMA-like protein. Preferably, the DNA fragment has the sequence shown in SEQ ID No. 1 or fragments thereof, and the PSMA-like protein has the amino acid sequence shown in SEQ ID No. 2 or fragment thereof.

In a preferred embodiment, there is provided a vector and/or a host cell comprising the above-disclosed DNA fragment. Further preferably, the host cell can be a bacterial cell, a mammalian cell, a plant cell or an insect cell.

In another embodiment of the present invention, there is provided an isolated and purified PSMA-like protein coded for by DNA selected from the group consisting of (a) isolated DNA which encodes a PSMA-like protein; (b) isolated DNA which hybridizes to the isolated DNA of (a) and which encodes a PSMA-like protein; and (c) isolated DNA differing from the isolated DNAs from (a) and (b) in codon sequence due to the degeneracy of the genetic code, and which encodes a PSMA-like protein. Preferably, the PSMA-like protein has an amino acid sequence shown in SEQ ID No. 2 or fragments thereof.

In a preferred embodiment, there is provided an antibody directed against the PSMA-like protein disclosed herein.

In still another embodiment of the present invention, there is provided a method of distinguishing prostate specific membrane antigen gene expression from prostate specific membrane antigen-like gene expression, comprising the steps of: (a) contacting a sample with one or more oligonucleotide primer(s) under hybridizing conditions, wherein the sample comprises RNA; (b) performing RT-PCR on the sample, thereby producing RT-PCR products; (c) contacting the RT-PCR products with an appropriate restriction enzyme, thereby producing digested RT-PCR products; and (d) analyzing the digested RT-PCR products, wherein PSMA gene expression is distinguished from PSMA-like gene expression by detection of fragment size(s) in the digested RT-PCR products, wherein digested PSMA-specific RT-PCR products comprise different predicted fragment size(s) compared with digested PSMA-like-specific RT-PCR products. Preferably, the oligonucleotide primer is selected from the group consisting of SEQ ID Nos. 5–38. Representative restriction enzymes are EcoRI and AccI. Additionally, restriction enzymes such as Bsp1286I, Sse9I, Tsp509I, TspEI, TspRI, Bst1107I, AciI, MspAI, NspBII, RsaI, HaeIII or SspI may be utilized. Representative samples are blood cells, cells growing in culture, biopsied cells, epithelial cells, endothelial cells, urine and seminal fluid.

For example, when the oligonucleotide primers are SEQ ID No. 37 and SEQ ID No. 38, and the restriction enzyme is EcoRI, presence of fragment sizes of 348 nucleotides and 207 nucleotides indicates PSMA gene expression in the sample, while presence of fragment size of 555 nucleotides indicates PSMA-like gene expression in the sample. Alternatively, when the restriction enzyme is AccI, presence of fragment sizes of 506nuclotides and 49 nucleotides indicates prostate specific membrane antigen gene expression in the sample and presence of fragment sizes 319 nucleotides, 187 nucleotides and 49 nucleotides indicates PSMA-like gene expression in the sample.

In yet another embodiment of the present invention, there is provided a method of distinguishing prostate specific membrane antigen protein from prostate specific membrane antigen-like protein in a sample, comprising the steps of: (a) contacting the sample with at least one antibody specific for a PSMA protein and/or at least one antibody specific for a PSMA-like protein under appropriate conditions; and (b) detecting binding of the antibody or antibodies. The specificity of binding is indicative of the presence of prostate specific membrane antigen and/or PSMA-like proteins in the sample. Preferably, the antibody specific for a prostate specific membrane antigen protein is specific for a region of the PSMA protein and does not cross-react with a PSMA-like protein, or alternatively, the antibody specific for a PSMA-like protein is specific for a region of the PSMA-like protein and does not cross-react with a prostate specific membrane antigen protein. Representative means of detection are colorimetric assay, fluorescence, radioautography, nuclear medicine detection, electron microscopy, enzymatic assays, enzyme-linked immunoassays and MRI.

In yet another embodiment of the present invention, there is provided a vector for targeted gene therapy, comprising: a promoter/enhancer region from a PSMA gene or a PSMA-like gene; and a therapeutic gene. PSMA gene promoterlenhancer targets the therapeutic gene to prostate tissues and tumor neovasculature of solid tumors, whereas PSMA-like gene promoter/enhancer targets to non-prostate tissues.

In still yet another embodiment of the present invention, there is provided a method of screening for prostate specific membrane antigen or prostate specific membrane antigen-like ligands, comprising the steps of contacting a PSMA or PSMA-like protein, or fragment thereof, with potential ligands under conditions that permit protein—protein binding; removing non-specific protein—protein binding; and eluting protein bound to the PSMA or PSMA-like protein. Typically, the eluted protein is a ligand for the PSMA or PSMA-like protein.

Also provided in another embodiment of the present invention is a method of imaging cells expressing a prostate specific membrane antigen or prostate specific membrane antigen-like protein, comprising the steps of: administering to the cells at least one compound, wherein the compound is specifically directed towards a PSMA or PSMA-like protein and labeled with an imaging agent; and detecting the imaging agent in the cells. Preferably, the compound directed towards a PSMA or PSMA-like protein is an antibody or a ligand.

Still provided in an embodiment of the present invention is a cytotoxic composition, comprising: a compound specific for either a prostate specific membrane antigen protein or fragment thereof, or a prostate specific membrane antigen-like protein or fragment thereof; and a cytotoxic agent. Preferably, the compound directed towards a PSMA or PSMA-like protein is an antibody or a ligand. Preferably, the cytotoxic agent is a radioisotope or a toxin. The antibody may be linked to the cytotoxic agent either chemically or genetically. For example, the gene encoding the antibody may be fused to the gene encoding the cytotoxic agent.

Further provided is a pharmaceutical composition comprising an antibody directed against a PSMA protein and does not recognize a PSMA-like protein. Such composition can be used for diagnosing a cancer or a neurological disorder in an individual by detecting the localization of the antibody, wherein the detection of the antibody indicates a possibility of having a cancer or a neurological disorder. Representative examples of cancer include a prostate cancer, a bladder cancer, a pancreatic cancer, a sarcoma, a melanoma, a lung cancer and a kidney cancer. A representative example of a neurological disorder is schizophrenia.

Further provided is a method of inducing cell death in a cell by transfecting said cell with a vector expressing PSMA-like protein. In a preferred embodiment, the cell is a prostrate cancer cell such as PC3 prostrate cells.

Also provided are methods for inhibiting cell death. These methods may comprise inhibiting PSMA-like gene expression in a cell. Alternatively, an inhibitor of PSMA-like protein may be administered to a cell.

In accordance with the present invention, there may be employed conventional molecular biology, microbiology, and recombinant DNA techniques within the skill of the art. Such techniques are explained fully in the literature. See, e.g., Sambrook, Fritsch & Maniatis, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription and Translation" [B. D. Hames & S. J. Higgins eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984). Therefore, if appearing herein, the following terms shall have the definitions set out below.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure herein according to the normal convention of giving only the sequence in the 5' to 3' direction along the nontranscribed strand of DNA (i.e., the strand having a sequence homologous to the mRNA).

A "vector" is a replicon, such as plasmid, phage or cosmid, to which another DNA segment may be attached so as to bring about the replication of the attached segment. A "replicon" is any genetic element (e.g., plasmid, chromosome, virus) that functions as an autonomous unit of DNA replication in vivo; i.e., capable of replication under its own control. An "origin of replication" refers to those DNA sequences that participate in DNA synthesis. An "expression control sequence" is a DNA sequence that controls and regulates the transcription and translation of another DNA sequence. A coding sequence is "operably linked" and "under the control" of transcriptional and translational control sequences in a cell when RNA polymerase transcribes the coding sequence into mRNA, which is then translated into the protein encoded by the coding sequence.

Expression vectors containing promoter sequences that facilitate the efficient transcription and translation of the inserted DNA fragment are used in connection with the host. The expression vector typically contains an origin of replication, promoter(s), terminator(s), as well as specific genes which are capable of providing phenotypic selection in transformed cells. The transformed hosts can be fermented and cultured according to means known in the art to achieve optimal cell growth.

A DNA "coding sequencer" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include prokaryotic sequences, cDNA from eukaryotic mRNA, genomic DNA sequences from eukaryotic DNA, and even synthetic DNA sequences. A polyadenylation signal and transcription termination sequence will usually be located 3' to the coding sequence. A "cDNA" is defined as copy-DNA or complementary-DNA, and is a product of a reverse transcription reaction from an mRNA transcript. An "exon" is an expressed sequence transcribed from the gene locus, whereas an "intron" is a non-expressed sequence that is from the gene locus. As used in the present invention, "exons" of PSMA-like gene are referred to regions of genomic DNA in the PSMA-like gene that are homologous to known exons in the PSMA gene; and "introns" of PSMA-like gene are referred to the regions of genomic DNA in the PSMA-like gene that are homologous to known introns in the PSMA gene.

Transcriptional and translational control sequences are DNA regulatory sequences, such as promoters, enhancers, polyadenylation signals, terminators, and the like, that provide for the expression of a coding sequence in a host cell. As used herein, an "enhancer", "enhancer element" or "enhancer region" is a region separate from, or included with, a promoter element that typically enhances transcription or provides specific elements necessary from proper transcription. Enhancers typically can act at a distance, and often at either the 3' or 5' end of a gene. A "cis-element" is a nucleotide sequence, also termed a "consensus sequence" or "motif", that interacts with other proteins which can upregulate or downregulate expression of a specific gene locus. A "signal sequence" can also be included with the coding sequence. This sequence encodes a signal peptide, N-terminal to the polypeptide, that communicates to the host cell and directs the polypeptide to the appropriate cellular location. Signal sequences can be found associated with a variety of proteins native to prokaryotes and eukaryotes.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains (consensus sequences) responsible for the binding of RNA polymerase. Eukaryotic promoters often contain "TATA" boxes and "CAAT" boxes. Prokaryotic promoters contain Shine-Dalgarno sequences in addition to the −10 and −35 consensus sequences. As used herein, an enhancer element or region may be included with the minimal promoter elements required for transcription, to thereby create an expression pattern very similar to the native gene(s).

The term "oligonucleotide" is defined as a molecule comprised of two or more deoxyribonucleotides, preferably more than three. Its exact size will depend upon many factors which, in turn, depend upon the ultimate function and use of the oligonucleotide. The term "primer" as used herein refers to an oligonucleotide, whether occurring naturally, as in a purified restriction digest, or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and the method used. For example, for diagnostic applications, depending on the complexity of the target sequence, the oligonucleotide primer typically contains 15–25 or more nucleotides, although it may contain fewer nucleotides.

Primers are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence or hybridize therewith and thereby form the template for the synthesis of the extension product. Additionally, a single base difference in a primer, particularly at the 3' end from which extension occurs, is sufficient to allow differential hybridization of the two primers, thereby allowing selected amplification based upon a single site difference. As used herein, the terms "restriction endonucleases" and "restriction enzymes" refer to enzymes which cut double-stranded DNA at or near a specific nucleotide sequence.

"Recombinant DNA technology" refers to techniques for uniting two heterologous. DNA molecules, usually as a result of in vitro ligation of DNAs from different organisms. Recombinant DNA molecules are commonly produced by experiments in genetic engineering. Synonymous terms include "gene splicing", "molecular cloning" and "genetic engineering". The product of these manipulations results in a "recombinant" or "recombinant molecule".

A cell has been "transformed" or "transfected" with exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a vector or plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or ancestor by mitosis. A "cell line" is a clone of a primary cell that is capable of stable growth in vitro for many generations.

As used herein, the term "host" is meant to include not only prokaryotes but also eukaryotes such as yeast, plant and animal cells. A recombinant DNA molecule or gene can be used to transform a host using any of the techniques commonly known to those of ordinary skill in the art. Prokaryotic hosts may include *E. coli, S. tymphimurium, Serratia marcescens* and *Bacillus subtilis*. Eukaryotic hosts include yeasts such as *Pichia pastoris*, mammalian cells and insect cells, and more preferentially, plant cells, such as *Arabidopsis thaliana* and *Tobaccum nicotiana*.

Two DNA sequences are "substantially homologous" when at least about 75% (preferably at least about 80%, and most preferably at least about 90% or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. In another example, the coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

As used herein, "fragment", as applied to a polypeptide, will ordinarily be at least 10 residues, more typically at least 20 residues, and preferably at least 30 (e.g., 50) residues in length, but less than the entire, intact sequence. Fragments can be generated by methods known to those skilled in the art, e.g., by enzymatic digestion of naturally occurring or recombinant protein, by recombinant DNA techniques using an expression vector that encodes a defined fragment, or by chemical synthesis. The ability of a candidate fragment to exhibit characteristics of a particular enzyme (e.g., binding to a specific antibody, or exhibiting partial enzymatic or catalytic activity) can be assessed by methods described herein. Purified fragments or antigenic fragments can be used to generate new regulatory enzymes using multiple functional fragments from different enzymes, as well as to generate antibodies, by employing standard protocols known to those skilled in the art.

A standard Northern blot assay can be used to ascertain the relative amounts of mRNA in a cell or tissue obtained from transgenic tissue, in accordance with conventional Northern hybridization techniques known to those persons of ordinary skill in the art. Similarly, a dot blot procedure or an RNAse protection assay can be used to evaluate the levels of mRNA expression. Alternatively, a standard Southern blot assay may be used to confirm the presence and the copy number of the gene in transgenic systems, in accordance with conventional Southern hybridization techniques known to those of ordinary skill in the art. The Northern blot, dot blot and Southern blot use a hybridization probe, e.g. radiolabeled cDNA, either containing the full-length, single stranded DNA or a fragment of the DNA sequence at least 20 (preferably at least 30, more preferably at least 50, and most preferably at least 100 consecutive nucleotides in length). The DNA hybridization probe can be labeled by any of the many different methods known to those skilled in this art.

The labels most commonly employed for these studies are radioactive elements, enzymes, chemicals which fluoresce when exposed to ultraviolet light, and others. A number of fluorescent materials are known and can be utilized as labels. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate. Proteins can also be labeled with a radioactive element or with an enzyme. The radioactive label can be detected by any of the currently available counting procedures. The preferred isotope may be selected from $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$.

Enzyme labels are likewise useful, and can be detected b y any of the presently utilized immunoenzymatic, calorimetric, spectrophotometric, fluorospectrophotometric, amperometric or gasometric techniques. Furthermore, the PSMA or PSMA-like enzymes can be labeled and the endogenous activities assayed. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090, 3,850,752, and 4,016,043 are referred to by way of example for their disclosure of alternate labeling material and methods.

The following examples are given for the purpose of illustrating various embodiments of the invention and are not meant to limit the present invention in any fashion:

EXAMPLE 1

Differentiating the PSMA Gene from the PSMA-like Gene

Figure 1B:
Figure 1C:

To map the human PSMA gene and resolve the controversy regarding its true location (11p versus 11q), a number of primer pairs were designed with homology to various regions of the PSMA gene, including introns. These primers were then used to amplify DNA from the NIGMS somatic cell hybrid mapping panel which consists of a hybrid containing chromosome 11, one containing chromosome 11p, one containing 11q and a hamster parental line. While the amplified regions of exon 16, intron n-o (primers used correspond to nt 54278-54536 in the PSMA genomic sequence and encompass exon 15 of the PSMA gene) and intron 6 are found on both chromosome 11p and 11q, the promoter region of the PSMA gene is only amplified from the hybrid containing chromosome 11p (see FIGS. 1A-1C). The fact that intron sequences are present also confirms that the gene on chromosome 11q is not a pseudogene, but in fact, a gene duplication.

Intron-based primers were then used to amplify and subsequently clone regions from the 11p and 11q genes. The existence of sequence differences between the two genes was confirmed by analysis of the corresponding regions in four normal DNA samples. Based on the number of single base differences between non-coding regions of the two genes, it is estimated that the gene duplication occurred 22 million years ago, after the divergence of man and mouse. Taken together with data from the mouse model (i.e. only one gene corresponding to the PSMA gene family is present and maps to a region that corresponds to human chromosome 11q), it is expected that the 11q gene (the PSMA-like gene) is the ancestral gene, and therefore, is likely to be functional. The fact that the promoter region of the PSMA-like gene was not subject to duplication implies at least a differential expression pattern for the two genes, which is also supported by the fact that the mouse homologue of PSMA-like gene is not expressed in the prostate.

Figure 2:
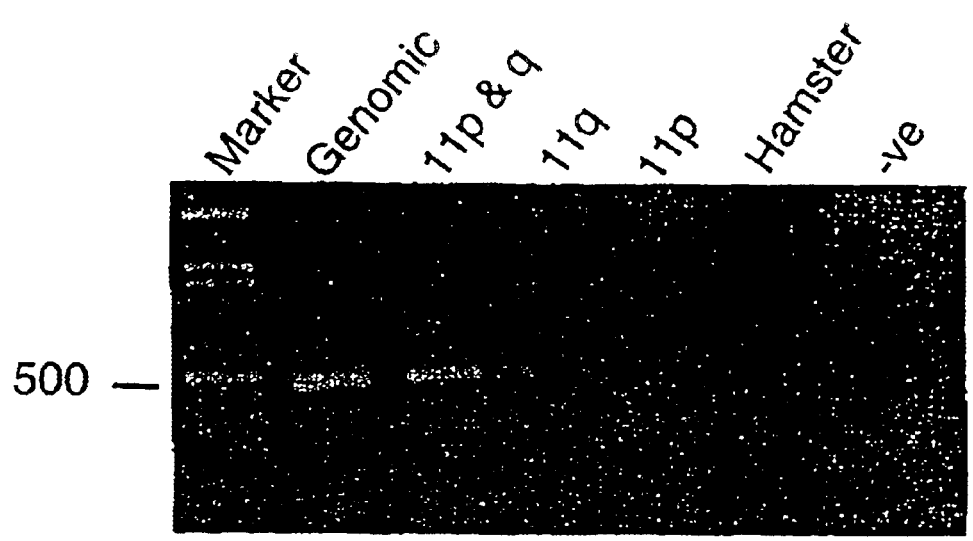
FIG. 2 shows specific amplification of the 11q PSMA-like gene using primers designed by sequence analysis of the 11 q gene.

Based on sequence differences between the human PSMA and PSMA-like genes, primer sequences (sense, 5'-GCCTTCATTTTCAGAACATCTCATGCAT-3', SEQ ID No. 5; antisense, 5'-GTCCATATAAACTTTCAAGAATGTG-3', SEQ ID No. 6) were designed that only amplify the first intron of the PSMA-like gene on chromosome 11q (see FIG. 2). These primers are used to screen a human PAC library for the PSMA-like genomic clone.

EXAMPLE 2

Evidence for a Novel PSMA Splice Variant

Figure 3:
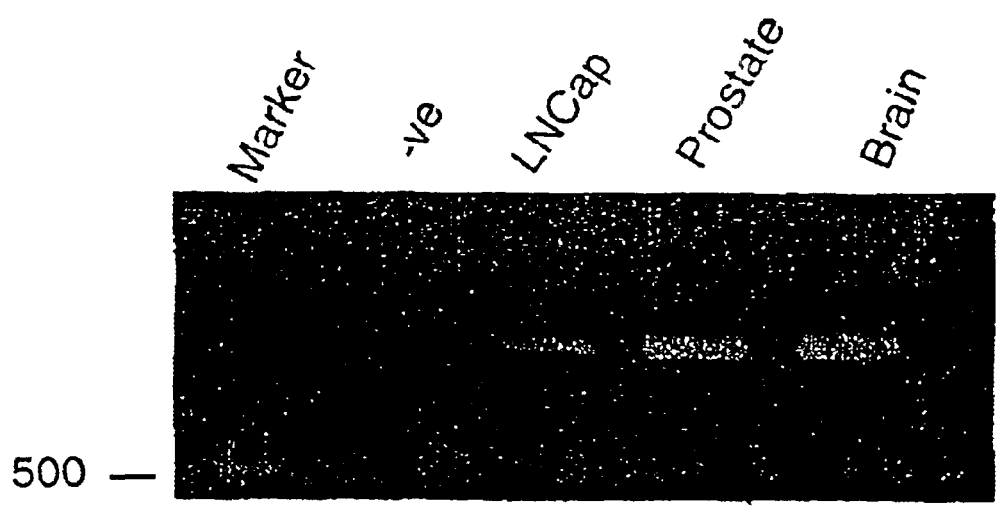
FIG. 3 shows amplification of the 3' end of prostate specific membrane antigen or PSMA-like mRNA using cDNA-specific primers with the cDNA derived from the indicated tissues. Note the lower band (splice variant) that is only present in LNCaP and prostate cells.

As analysis of the brain and prostate PSMA and PSMA-like genes was being carried out, RT-PCR of the terminal region of the PSMA gene detected an alternate splice form of PSMA present in LNCaP cells and normal prostate that is not present in normal brain (see FIG. 3). This appears to be a novel splice variant of PSMA and the expression pattern of this variant is evaluated in prostate and other tissues.

EXAMPLE 3

Screening for Ligands of PSMA/PSM'

It has previously been reported that mitochondrial aspartate-aminotransferase (mAAST) binds to PSMA, since it co-elutes with PSMA from affinity columns made with the 7E11C5.3 antibody [27]. Using a similar isolation method, co-elution with PSMA of a protein of the size expected for mAAST from LNCAP cells was demonstrated. However, this protein is apparently not a PSMA ligand, as it is also eluted from the same 7E11C5.3 affinity column that has been treated with protein lysate from non-PSMA expressing PC3 cells.

The yeast-two-hybrid system is also being used to screen for PSMA ligands. To date, six million clones have been screened from a prostate library and six different, consistently interacting clones have been identified. Significantly, one of the positive clones corresponds to Survivin, a recently cloned apoptosis inhibitor which is highly expressed in prostate tumors, but is not typically expressed in terminally differentiated adult tissues. A second clone identified in the screen corresponds to a gene whose sequence has been put in Genbank as part of the chromosome 22 sequencing project. All six clones will be subcloned into appropriate vectors for re-confirming the protein—protein interaction with PSMA in the mammalian-two-hybrid system.

EXAMPLE 4

Sequencing the PSMA-like Gene

For prostate specific membrane antigen to be useful as a therapeutic and clinical target for prostate cancers, it is necessary to be able to readily distinguish the various transcript and/or proteins from one another (i.e. PSM', PSMA and PSMA-like). Primers that specifically amplify the chromosome 11q PSMA-like gene are used to screen a human PAC library by PCR. The general insert size of a PAC is around 100 kb, and the PAC library is considered to have a three-fold coverage of the human genome. Sequence is obtained directly from the PAC using at least two primers to PCR amplify each of the 19 exons. The primers are designed using the PSMA cDNA exonic sequences. This approach ensures that every intron-exon boundary is examined.

EXAMPLE 5

Nucleotide differences Between the PSMA and PSMA-like Genes

Of the 19 exons in the PSMA-like gene, 18 have been sequenced. Oligonucleotide primers based upon intronic sequences of the PSMA genomic clone (GenBank Accession No. AF007544) (Table 1) were used to amplify the corresponding regions of the PSMA-like gene from somatic cell hybrids containing human chromosome 11q (i.e. Hybrids GM11936 and GM07298 from Coriell Cell Repositories, N J). The amplified PCR products were then purified, sequenced and compared to the cDNA sequence of the PSMA gene (GenBank Accession No. M99487). The nucleotide and amino acid differences obtained for exons 2–19 are described in Table 2. In the case of exon 19, the sequence was confirmed by 3' RACE, which also confirmed that the mRNA transcript of the PSMA-like gene ends in the same place as that of the PSMA gene.

TABLE 1

| Exon | Bases | Sense Primer | Sense Primer Sequence | Antisense Primer | Antisense Primer sequence | PCR product size expected |
|---|---|---|---|---|---|---|
| 1 | 2488–2863 | | | | | |
| 2 | 4994–5099 | 4870 | ctcacctaatgtcagaggta (SEQ ID No. 7) | 5254 | agtatagtcctcctcagatg (SEQ ID No. 8) | 384 |
| 3 | 10726–10912 | 10630 | caaagtacttttgtgtaactctgc (SEQ ID No. 9) | 11082 | cataggaaagtagttgacacgg (SEQ ID No. 10) | 452 |
| 4 | 18275–18376 | 18157 | cctgaaggattcattcaccctc (SEQ ID No. 11) | 18457 | gaccctttaattatcggctgaaca (SEQ ID No. 12) | 300 |
| 5–6 | 24400–25500 | 24323 | atgtccaacagtccccatgcag (SEQ ID No. 13) | 25593 | gacatgcttagtccattgtacc (SEQ ID No. 14) | 1270 |

TABLE 1-continued

| Exon | Bases | Sense Primer | Sense Primer Sequence | Anti-sense Primer | Antisense Primer sequence | PCR product size expected |
|---|---|---|---|---|---|---|
| 7 | 27927–28020 | 27871 | gaaccgtttgaatgaaactgag (SEQ ID No. 15) | 28058 | ttacccaaatagccatccatgg (SEQ ID No. 16) | 187 |
| 8–9 | 35216–36281 | 35127 | gcagatgctcaataagtgaatcc (SEQ ID No. 17) | 36334 | ccagcacataacagttacttgatc (SEQ ID No. 18) | 1207 |
| 10 | 37697–37816 | 37619 | tagatgctattgagtcgtttgc (SEQ ID No. 19) | 37867 | aaactgagactcagataggctg (SEQ ID No. 20) | 248 |
| 11 | 39896–39978 | 39825 | ctgggcttggtagtgtcctggg (SEQ ID No. 21) | 40045 | gcttggcaaacaagtcctggctac (SEQ ID No. 22) | 220 |
| 12 | 41911–41974 | 41792 | tgtcgttaatatgggtcagctc (SEQ ID No. 23) | 42035 | ttaactagactgctgctcctag (SEQ ID No. 24) | 243 |
| 13 | 46402–46469 | 46317 | tggtaggaatttagcagtggtc (SEQ ID No. 25) | 46687 | gatgctactaatgggctacctc (SEQ ID No. 26) | 370 |
| 14 | 53129–53220 | 53053 | cttctggttaatggacatctag (SEQ ID No. 27) | 53264 | caatcccacactgaattcagtg (SEQ ID No. 28) | 211 |
| 15 | | | agaatggggtttagtttaatgg (SEQ ID No. 29) | | tgagtcactttttggagtcag (SEQ ID No. 30) | |
| 16–17 | 56661–57307 | 56614 | ttgtaagctatccctataagag (SEQ ID No. 31) | 57393 | agttcagcaacagtcatgttag (SEQ ID No. 32) | 779 |
| 18 | 62423–62515 | 62305 | gggtggtcctgaaaccaatccc (SEQ ID No. 33) | 62553 | gtgatattacagaaaggagtc (SEQ ID No. 34) | 248 |
| 19 | 64209–64518 | 64127 | atccaggaattgcagagtgctc (SEQ ID No. 35) | 64586 | ttcagttta atccatagggag (SEQ ID No. 36) | 459 |

TABLE 2

| Exon # in PSMA gene | Nucleotide changes PSMA→PSMA-like | Amino acid changes PSMA→PSMA-like |
|---|---|---|
| 2 | No change | No change |
| 3 | nt 630  t→a | Thr→Thr |
|   | nt 584  t→c | Val→Ala |
|   | nt 594  a→t | Ala→Ala |
| 4 | nt 739  c→t | Pro→Ser |
| 5 | nt 777  c→t | Gly→Gly |
|   | nt 787  t→c | Tyr→His |
|   | nt 877  g→a | Gly→Arg |
| 6 | nt 948  c→t | Ser→Ser |
|   | nt 993  t→c | Asp→Asp |
|   | nt 1023 g→t | Gln→His |
| 7 | nt 1092 t→c | Tyr→Tyr |
|   | nt 1103 g→a | Arg→Gln |
|   | nt 1150 a→g | Ile→Val |
| 8 | nt 1237 c→t | Pro→Ser |
| 9 | nt 1320 a→g | Thr→Thr |
| 10 | nt 1454 t→c | Ile→Thr |
| 11 | No change | No change |
| 12 | nt 1572 g→t | Glu→Asp |
| 13 | nt 1665 g→a | Pro→Pro |
|   | nt 1684 c→t | His→Tyr |
| 14 | No change | No change |
| 15 | No change | No change |
| 16 | nt 2099 g→a | Ser→Asn |
|   | nt 2140 g→t | Val→Leu |
| 17 | nt 2172 g→a | Lys→Lys |
|   | nt 2202 t→c | Ser→Ser |
| 18 | nt 2239 g→t | |
|   | nt 2241 a→g | Val→Leu |
|   | nt 2314 g→a | Arg→Arg |
| 19 | nt 2442 a→t | Glu→Asp |
|   | nt 2459 a→c | Tyr→Ser |
|   | nt 2531 a→c | No change (3' UTR) |
|   | nt 2534 c→t | No change (3' UTR) |
|   | nt 2562 AG is deleted in PSMA-like gene | No change (3' UTR) |
|   | nt 2571 c→a | No change (3' UTR) |
|   | nt 2572 g→a | No change (3' UTR) |

EXAMPLE 6
Sequences of PSMA-like Gene and Protein

PSMA-like gene was isolated from a liver library and sequenced. The complete sequence is shown in SEQ ID No. 1, whereas the predicted amino acid sequence of PSMA-like protein is shown in SEQ ID No. 2. The alignment between PSMA and PSMA-like proteins are shown in FIGS. 4A and 4B. It seems that the PSMA-like starts transcribing in the middle of intron 6 (compared to PSMA). It therefore results in a smaller protein, which is significantly different from PSMA. The similarity of the homologous regions of the two genes is around 98% at the amino acid level. PSMA-like protein will be tested for enzyme activity.

EXAMPLE 7
Tissue Distribution of the PSMA-like Gene

PCR on cDNAs from various tissues was performed using the following primer sequences:

Primer 1: 5' ACAGATATGTCATTCTGGGAGGTC 3' (SEQ ID No. 37) (sense; exon 10)

Primer 2: 5' ACTGTGATACAGTGGATAGCCGCT 3' (SEQ ID No. 38) (anti-sense; exon 16)

PCR was run at 94° C. for 3.5 min, 94° C. for 20 sec, 61° C. for 20 sec, and 72° C. for 50 sec for 35 cycles. The expected size after PCR amplification from both PSMA and PSMA-like RNA is 555 base pairs.

One fifth of the reaction was then digested with EcoRI or AccI. After 1–3 hours of digestion, the product was electrophoresed and photographed. If the product was digested with EcoRI and fragments of 348 and 207 nucleotides are produced, then PSMA mRNA was present in the original sample. If an undigested, single band of 555 nucleotides is present following EcoRI digestion, PSMA-like RNA was present in the sample. If the product was digested with AccI, bands of 506 and 49 nucleotides are expected if the original sample expressed the PSMA gene, and 319, 187 and 49 nucleotides if the PSMA-like gene was expressed.

RT-PCR analysis has shown that the PSMA gene is expressed in the vasculature of almost all solid tumors examined so far (>10), including bladder cancer, pancreatic cancer, sarcomas, melanomas, lung cancer, kidney cancer, as well as the prostate. The PSMA-like gene is expressed in kidney and liver. Some tissues exhibit all bands expected, meaning that both the PSMA and PSMA-like genes are expressed.

This method can be used to amplify other regions of the PSMA and PSMA-like gene that differ in nucleotide sequence. Numerous combinations of primers are acceptable, providing the primers hybridize to both the PSMA and PSMA-like genes and amplify a region that differs between the two genes such that restriction analysis of the product will differentiate between the genes. For example, in exon 8, Bsp12861 restricts PSMA but not PSMA-like DNA; in exon 10, the PSMA gene, but not the PSMA-like gene, is digested by Sse9I, Tsp509I or TspEI; in exon 12, PSMA is digested by EcoRI, while PSMA-like is not; in exon 13, PSMA-like DNA, but not PSMA DNA, is digested by TspRI, AccI or Bst1107I and PSMA DNA, but not PSMA-like DNA is digested by AciI, MspAI, NspBII or RsaI; in exon 18, PSMA is restricted by HaeIII, while PSMA-like DNA is digested by SspI. This list is not meant to be all inclusive, but provides numerous restriction sites specific to either the PSMA or PSMA-like genie for differential identification and analysis.

EXAMPLE 8
Differential Genetic Marker or Restriction Site Polymorphism

To confirm that the EcoRI restriction enzyme site actually differed between the two genes and was not due to a polymorphism of the PSMA gene within the population, DNA obtained from more than 15 different people was amplified using PCR primers spanning this restriction site and subsequently digested with EcoRI. The presence of 3 bands after digestion indicated that all the people tested had both the PSMA and PSMA-like genes, and that those genes could be distinguished by the EcoRI site. This result is evidence that the EcoRI site is not a polymorphism, but is instead a genetic marker for distinguishing the PSMA gene from the PSMA-like gene.

EXAMPLE 9
NAALADase Enzymatic Activity of PSMA-like Protein

The PSMA-like clone obtained from screening the liver cDNA library was excised and cloned into the pIRES-neo vector (Clontech). PC-3 cells, which do not express PSMA, PSMA-like or have NAALADase activity were then transfected with the PSMA-like-neo vector using Lipofectamine Plus (Gibco-BRL) [9]. Transfected cells stably expressing the PSMA-like gene were then selected for by growing them in 1000 ug/ml Geneticin. Protein was isolated from the cell lines by lysing them in 50 mM Tris-HCl pH 7.4, 0.5% Triton X-100. 2 μg of protein was incubated with 20 μM tritiated NAAG in a total volume of 100 μl of lysis buffer for one hour. The substrate and its cleaved by-products were separated via ion-exchange chromatography and tritiated glutamate was eluted from the column in 1 M formic acid and quantified by counting in a scintillation counter. Control experiments included C4-2 LNCaP cells (positive control) and PC-3 cells that had been transfected with the pIRES-neo vector alone.

Figure 5:
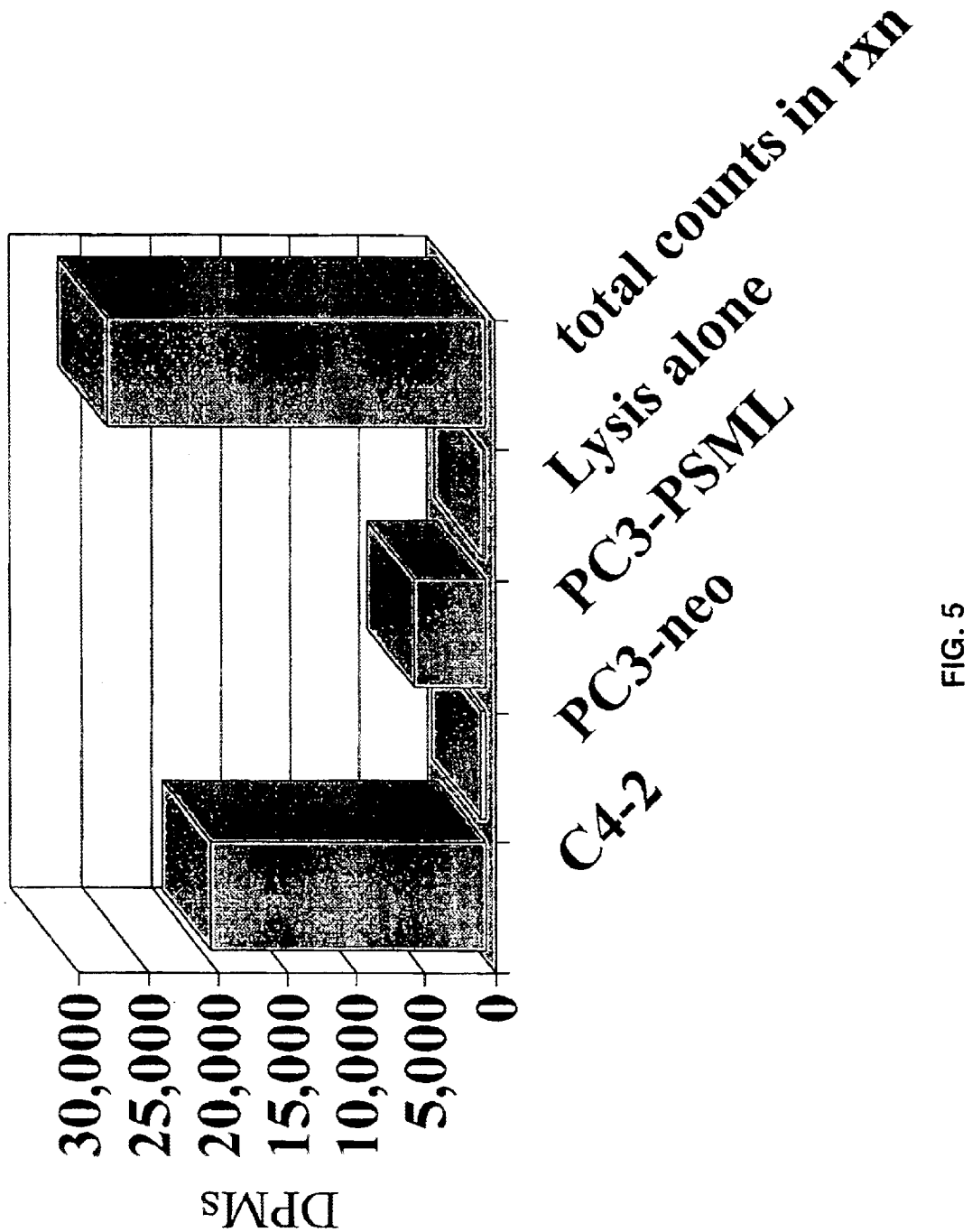
FIG. 5 shows the NAALADase enzymatic activity of PSMA-like protein.

The data shows that cells transfected with the PSMA-like vector have nearly 15 fold over that seen with the cells transfected with vector alone (background counts, FIG. 5). Thus PSMA-like does have NAALADase activity, and should be taken into account when designing prodrug strategies targeting PSMA. NAALADase enzymatic activity suggests that PSMA-like may be able to b e secreted to the serum/urine/seminal fluid, and that differentiating PSMA-like and PSMA proteins may make all the difference in diagnosis. For example, PSMA-like protein may be used for diagnosing neurological disorders such as schizophrenia.

EXAMPLE 10
Expression of PSMA Induces Cell Death in Prostrate Cancer Cells

PC3 (prostate cancer) cells were transfected with one of the following constructs: 1) pIRES-neo™ (Clontech) expression vector containing no inserted DNA; 2) pIRES-neo™ PSMA, consisting of the pIRES-neo™ vector expressing PSMA under the control of the CMV promoter; 3) pIRES-neo™ PSMA-Like, consisting of the pIRES-neo™ vector containing the full-length PSMA-Like gene instead of PSMA; and, 4) pIRES-neo™ hybrid, the same expression vector encoding a 750 amino acid "hybrid" PSMA—PSMA like molecule consisting of 308 amino acids corresponding to the first 308 of PSMA followed by 442 amino acids corresponding to the entire protein coding region of the PSMA-Like gene. The transfections were performed using Lipofectamine 2000™ (Invitrogen) liposomes according to the manufacturer's instructions. In addition, all constructs were co-transfected with the pAdVAntage™ vector (Promega), according to the manufacturer's instructions. pAdVAntage™ maximizes expression of the co-transfected molecules. Transfection efficiency, as determined via replica transfections with GFP-expressing plasmids, indicated approximately 80% of the cells were transfected.

Twenty-four hours post-transfection, cells were washed in PBS and randomly (blindly) chosen fields were photographed. Representative fields of PC3 cells transfected with each of the four vectors are shown in FIG. 6. From these results, it was concluded that expression of the PSMA-Like gene in PC3 cell induces cell death. This cell death is rapid, occurring by 24 hours post-transfection. This "death" effect of the gene does not seem to depend on enzymatic activity of the protein (data not show). Inappropriate expression of the PSMA-like gene in certain cell types is likely to induce disease by causing excessive cell death. For example, inappropriate expression of the PSMA-like gene in brain cells may be a factor in the development of schizophrenia.

The following references were cited herein:
[1] D. A. Silver, et al, Clin. Cancer Res. 3 (1997) 81–85.
[2] M. Kawakami, et al, Cancer Res. 57 (1997) 2321–2324.
[3] G. L. Wright Jr., et al, Urol. Oncol. 1 (1995)18–28.
[4] R. S. Israeli, et al, Cancer Res. 54 (1994)1807–1811.
[5] S. L. Su, et al, Cancer Res. 55 (1995) 1441–1443.
[6] H. Liu, et al, Cancer Res. 57 (1997) 3629–3634.
[7] R. E. Carter, et al, Proc. Natl. Acad. Sci. 93 (1996) 749–753.
[8] C. W. Rinker-Schaeffer, et al, Genomics. 30 (1995) 105–108.
[9] D. S. O'Keefe, et al. Biochimica Biophysica Acta. (1998) 1443:113–127.
[10] Luthi-Carter, et al. J. Pharm. Exp. Ther. 286 (1998) 1020–1025.
[11] Y. Kimoto, Mol. Gen. Genet. 258 (1998) 233–239.
[12] J. L. Gala, et al. Clin. Chem. 44 (1998) 472–481.
[13] J. T. Pinto, et al. Clin. Cancer Res. 2 (1996) 1445–1451.
[14] W. D. W. Heston. Mol. Urol. 1 (1997) 11–20.
[15] Liu H, et al Cancer Res. (1998) 58:4055–60.

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. An isolated DNA encoding a mammalian prostate specific membrane antigen-like protein, wherein said protein has the amino acid sequence of SEQ ID NO. 2.

2. The isolated DNA of claim 1, wherein said DNA has the sequence shown in SEQ ID No. 1.

3. A vector comprising the DNA of claim 1 and regulatory elements necessary for expression of the DNA in a cell.

4. A host cell comprising the vector of claim 3, wherein said vector is introduced into said host cell in vitro.

5. The host cell of claim 4, wherein said cell is selected from the group consisting of a bacterial cell, a mammalian cell, a plant cell and an insect cell.

* * * * *

SEQUENCE LISTING

<160> NUMBER OF SEQ ID NOS: 38

<210> SEQ ID NO 1
<211> LENGTH: 1992
<212> TYPE: DNA
<213> ORGANISM: Homo sapiens
<220> FEATURE:
<223> OTHER INFORMATION: cDNA sequence of PSMA-like gene

<400> SEQUENCE: 1

| | | | | | |
|---|---|---|---|---|---|
| agcaaatact | cactaccaca | aataagaaca | tttccaaatc | tgatgttctg | 50 |
| aggatttta | gagcttatag | tagcaaaaag | aaaagggaaa | ttctctctga | 100 |
| gatgtccttt | tttgtaggcc | taatgacaaa | aggttgaaga | taaagttcta | 150 |
| gtactcattt | aagtgtaata | ttgaaaattg | atattaccaa | atctggaaca | 200 |
| accaatttaa | aataaggaaa | gaaagacact | gtgttttcta | ggttaaaaat | 250 |
| gcccagctgg | caggggccaa | aggagtcatt | ctctactcag | accctgctga | 300 |
| ctactttgct | cctggggtga | agtcctatcc | agacggttgg | aatcttcctg | 350 |
| gaggtggtgt | ccagcgtgga | aatatcctaa | atctgaatgg | tgcaggagac | 400 |
| cctctcacac | caggttaccc | agcaaatgaa | tacgcttata | ggcatggaat | 450 |
| tgcagaggct | gttggtcttc | caagtattcc | tgttcatcca | gttggatact | 500 |
| atgatgcaca | gaagctccta | gaaaaaatgg | gtggctcagc | accaccagat | 550 |
| agcagctgga | gaggaagtct | caaagtgtcc | tacaatgttg | gacctggctt | 600 |
| tactggaaac | ttttctacac | aaaaagtcaa | gatgcacatc | cactctacca | 650 |
| atgaagtgac | gagaatttac | aatgtgatag | gtactctcag | aggagcagtg | 700 |
| gaaccagaca | gatatgtcat | tctgggaggt | caccgggact | catgggtgtt | 750 |
| tggtggtatt | gaccctcaga | gtggagcagc | tgttgttcat | gaaactgtga | 800 |
| ggagctttgg | aacactgaaa | aaggaagggt | ggagacctag | aagaacaatt | 850 |
| ttgtttgcaa | gctgggatgc | agaagaattt | ggtcttcttg | gttctactga | 900 |
| gtgggcagag | gataattcaa | gactccttca | agagcgtggc | gtggcttata | 950 |
| ttaatgctga | ctcatctata | gaaggaaact | acactctgag | agttgattgt | 1000 |
| acaccactga | tgtacagctt | ggtatacaac | ctaacaaaag | agctgaaaag | 1050 |
| ccctgatgaa | ggctttgaag | gcaaatctct | ttatgaaagt | tggactaaaa | 1100 |
| aaagtccttc | cccagagttc | agtggcatgc | ccaggataag | caaattggga | 1150 |
| tctggaaatg | attttgaggt | gttcttccaa | cgacttggaa | ttgcttcagg | 1200 |
| cagagcacgg | tatactaaaa | attgggaaac | aaacaaattc | agcggctatc | 1250 |
| cactgtatca | cagtgtctat | gaaacatatg | agttggtgga | aagttttat | 1300 |
| gatccaatgt | ttaaatatca | cctcactgtg | gcccaggttc | gaggagggat | 1350 |
| ggtgtttgag | ctagccaatt | ccatagtgct | ccctttgat | tgtcgagatt | 1400 |

-continued

| | |
|---|---|
| atgctgtagt tttaagaaag tatgctgaca aaatctacaa tatttctatg | 1450 |
| aaacatccac aggaaatgaa gacatacagt ttatcatttg attcactttt | 1500 |
| ttctgcagta aaaaatttta cagaaattgc ttccaagttc agcgagagac | 1550 |
| tccaggactt tgacaaaagc aacccaatat tgttaagaat gatgaatgat | 1600 |
| caactcatgt ttctggaaag agcatttatt gatccattag ggttaccaga | 1650 |
| cagaccttt tataggcatg tcatctatgc tccaagcagc cacaacaagt | 1700 |
| atgcagggga gtcattccca ggaatttatg atgctctgtt tgatattgaa | 1750 |
| agcaaagtgg acccttccaa ggcctgggga gatgtgaaga gacagatttc | 1800 |
| tgttgcagcc ttcacagtgc aggcagctgc agagactttg agtgaagtag | 1850 |
| cctaagagga ttctttagag actctgtatt gaatttgtgt ggtatgtcac | 1900 |
| tcaaagaata ataatgggta tattgataaa ttttaaaatt ggtatatttg | 1950 |
| aaataaagtt gaatattata tataaaaaaa aaaaaaaaa aa | 1992 |

<210> SEQ ID NO 2
<211> LENGTH: 442
<212> TYPE: PRT
<213> ORGANISM: Homo sapiens
<220> FEATURE:
<223> OTHER INFORMATION: deduced amino acid sequence of PSMA-like
      protein

<400> SEQUENCE: 2

Met Gly Gly Ser Ala Pro Pro Asp Ser Ser Trp Arg Gly Ser Leu
                5                  10                  15

Lys Val Ser Tyr Asn Val Gly Pro Gly Phe Thr Gly Asn Phe Ser
                20                  25                  30

Thr Gln Lys Val Lys Met His Ile His Ser Thr Asn Glu Val Thr
                35                  40                  45

Arg Ile Tyr Asn Val Ile Gly Thr Leu Arg Gly Ala Val Glu Pro
                50                  55                  60

Asp Arg Tyr Val Ile Leu Gly Gly His Arg Asp Ser Trp Val Phe
                65                  70                  75

Gly Gly Ile Asp Pro Gln Ser Gly Ala Ala Val Val His Glu Thr
                80                  85                  90

Val Arg Ser Phe Gly Thr Leu Lys Lys Glu Gly Trp Arg Pro Arg
                95                  100                 105

Arg Thr Ile Leu Phe Ala Ser Trp Asp Ala Glu Glu Phe Gly Leu
                110                 115                 120

Leu Gly Ser Thr Glu Trp Ala Glu Asp Asn Ser Arg Leu Leu Gln
                125                 130                 135

Glu Arg Gly Val Ala Tyr Ile Asn Ala Asp Ser Ser Ile Glu Gly
                140                 145                 150

Asn Tyr Thr Leu Arg Val Asp Cys Thr Pro Leu Met Tyr Ser Leu
                155                 160                 165

Val Tyr Asn Leu Thr Lys Glu Leu Lys Ser Pro Asp Glu Gly Phe
                170                 175                 180

Glu Gly Lys Ser Leu Tyr Glu Ser Trp Thr Lys Lys Ser Pro Ser
                185                 190                 195

Pro Glu Phe Ser Gly Met Pro Arg Ile Ser Lys Leu Gly Ser Gly
                200                 205                 210

Asn Asp Phe Glu Val Phe Phe Gln Arg Leu Gly Ile Ala Ser Gly
                215                 220                 225

-continued

```
Arg Ala Arg Tyr Thr Lys Asn Trp Glu Thr Asn Lys Phe Ser Gly
            230                 235                 240

Tyr Pro Leu Tyr His Ser Val Tyr Glu Thr Tyr Glu Leu Val Glu
            245                 250                 255

Lys Phe Tyr Asp Pro Met Phe Lys Tyr His Leu Thr Val Ala Gln
            260                 265                 270

Val Arg Gly Gly Met Val Phe Glu Leu Ala Asn Ser Ile Val Leu
            275                 280                 285

Pro Phe Asp Cys Arg Asp Tyr Ala Val Val Leu Arg Lys Tyr Ala
            290                 295                 300

Asp Lys Ile Tyr Asn Ile Ser Met Lys His Pro Gln Glu Met Lys
            305                 310                 315

Thr Tyr Ser Leu Ser Phe Asp Ser Leu Phe Ser Ala Val Lys Asn
            320                 325                 330

Phe Thr Glu Ile Ala Ser Lys Phe Ser Glu Arg Leu Gln Asp Phe
            335                 340                 345

Asp Lys Ser Asn Pro Ile Leu Leu Arg Met Met Asn Asp Gln Leu
            350                 355                 360

Met Phe Leu Glu Arg Ala Phe Ile Asp Pro Leu Gly Leu Pro Asp
            365                 370                 375

Arg Pro Phe Tyr Arg His Val Ile Tyr Ala Pro Ser Ser His Asn
            380                 385                 390

Lys Tyr Ala Gly Glu Ser Phe Pro Gly Ile Tyr Asp Ala Leu Phe
            395                 400                 405

Asp Ile Glu Ser Lys Val Asp Pro Ser Lys Ala Trp Gly Asp Val
            410                 415                 420

Lys Arg Gln Ile Ser Val Ala Ala Phe Thr Val Gln Ala Ala Ala
            425                 430                 435

Glu Thr Leu Ser Glu Val Ala
            440
```

<210> SEQ ID NO 3
<211> LENGTH: 2653
<212> TYPE: DNA
<213> ORGANISM: Homo sapiens
<220> FEATURE:
<223> OTHER INFORMATION: nucleotide sequence of human PSMA gene
<300> PUBLICATION INFORMATION:
<308> DATABASE ACCESSION NUMBER: GenBank Accession No. M99487
<309> DATABASE ENTRY DATE: 1995-01-08

<400> SEQUENCE: 3

| | |
|---|---|
| ctcaaaaggg gccggatttc cttctcctgg aggcagatgt tgcctctctc | 50 |
| tctcgctcgg attggttcag tgcactctag aaacactgct gtggtggaga | 100 |
| aactggaccc caggtctgga gcgaattcca gcctgcaggg ctgataagcg | 150 |
| aggcattagt gagattgaga gagactttac cccgccgtgg tggttggagg | 200 |
| gcgcgcagta gagcagcagc acaggcgcgg gtcccgggag gccggctctg | 250 |
| ctcgcgccga gatgtggaat ctccttcacg aaaccgactc ggctgtggcc | 300 |
| accgcgcgcc gcccgcgctg gctgtgcgct ggggcgctgg tgctggcggg | 350 |
| tggcttcttt ctcctcggct tcctcttcgg gtggtttata aaatcctcca | 400 |
| atgaagctac taacattact ccaaagcata atatgaaagc atttttggat | 450 |
| gaattgaaag ctgagaacat caagaagttc ttatataatt ttacacagat | 500 |

-continued

| | |
|---|---|
| accacattta gcaggaacag aacaaaactt tcagcttgca aagcaaattc | 550 |
| aatcccagtg gaaagaattt ggcctggatt ctgttgagct agcacattat | 600 |
| gatgtcctgt tgtcctaccc aaataagact catcccaact acatctcaat | 650 |
| aattaatgaa gatggaaatg agattttcaa cacatcatta tttgaaccac | 700 |
| ctcctccagg atatgaaaat gtttcggata ttgtaccacc tttcagtgct | 750 |
| ttctctcctc aaggaatgcc agagggcgat ctagtgtatg ttaactatgc | 800 |
| acgaactgaa gacttcttta aattggaacg ggacatgaaa atcaattgct | 850 |
| ctgggaaaat tgtaattgcc agatatggga agttttcag aggaaataag | 900 |
| gttaaaaatg cccagctggc aggggccaaa ggagtcattc tctactccga | 950 |
| ccctgctgac tactttgctc ctggggtgaa gtcctatcca gatggttgga | 1000 |
| atcttcctgg aggtggtgtc cagcgtggaa atatcctaaa tctgaatggt | 1050 |
| gcaggagacc ctctcacacc aggttaccca gcaaatgaat atgcttatag | 1100 |
| gcgtggaatt gcagaggctg ttggtcttcc aagtattcct gttcatccaa | 1150 |
| ttggatacta tgatgcacag aagctcctag aaaaaatggg tggctcagca | 1200 |
| ccaccagata gcagctggag aggaagtctc aaagtgccct acaatgttgg | 1250 |
| acctggcttt actggaaact tttctacaca aaaagtcaag atgcacatcc | 1300 |
| actctaccaa tgaagtgaca agaatttaca atgtgatagg tactctcaga | 1350 |
| ggagcagtgg aaccagacag atatgtcatt ctgggaggtc accgggactc | 1400 |
| atgggtgttt ggtggtattg accctcagag tggagcagct gttgttcatg | 1450 |
| aaattgtgag gagctttgga acactgaaaa aggaagggtg gagacctaga | 1500 |
| agaacaatt tgttttgcaag ctgggatgca aagaatttg gtcttcttgg | 1550 |
| ttctactgag tgggcagagg agaattcaag actccttcaa gagcgtggcg | 1600 |
| tggcttatat taatgctgac tcatctatag aaggaaacta cactctgaga | 1650 |
| gttgattgta caccgctgat gtacagcttg gtacacaacc taacaaaaga | 1700 |
| gctgaaaagc cctgatgaag gctttgaagg caaatctctt tatgaaagtt | 1750 |
| ggactaaaaa aagtccttcc ccagagttca gtggcatgcc caggataagc | 1800 |
| aaattgggat ctggaaatga ttttgaggtg ttcttccaac gacttggaat | 1850 |
| tgcttcaggc agagcacggt atactaaaaa ttgggaaaca aacaaattca | 1900 |
| gcggctatcc actgtatcac agtgtctatg aaacatatga gttggtggaa | 1950 |
| aagttttatg atccaatgtt taaatatcac ctcactgtgg cccaggttcg | 2000 |
| aggagggatg gtgtttgagc tagccaattc catagtgctc cctttgatt | 2050 |
| gtcgagatta tgctgtagtt ttaagaaagt atgctgacaa aatctacagt | 2100 |
| atttctatga aacatccaca ggaaatgaag acatacagtg tatcatttga | 2150 |
| ttcacttttt tctgcagtaa agaattttac agaaattgct tccaagttca | 2200 |
| gtgagagact ccaggacttt gacaaaagca acccaatagt attaagaatg | 2250 |
| atgaatgatc aactcatgtt tctggaaaga gcatttattg atccattagg | 2300 |
| gttaccagac aggccttttt ataggcatgt catctatgct ccaagcagcc | 2350 |
| acaacaagta tgcaggggag tcattcccag gaatttatga tgctctgttt | 2400 |
| gatattgaaa gcaaagtgga cccttccaag gcctggggag aagtgaagag | 2450 |
| acagatttat gttgcagcct tcacagtgca ggcagctgca gagactttga | 2500 |

```
gtgaagtagc ctaagaggat tctttagaga atccgtattg aatttgtgtg           2550
gtatgtcact cagaaagaat cgtaatgggt atattgataa attttaaaat           2600
tggtatattt gaaataaagt tgaatattat ataaaaaaa aaaaaaaaaa            2650 aaa                                                              2653
```

<210> SEQ ID NO 4
<211> LENGTH: 750
<212> TYPE: PRT
<213> ORGANISM: Homo sapiens
<220> FEATURE:
<223> OTHER INFORMATION: deduced amino acid sequence of PSMA protein

<400> SEQUENCE: 4

```
Met Trp Asn Leu Leu His Glu Thr Asp Ser Ala Val Ala Thr Ala
                5                  10                  15

Arg Arg Pro Arg Trp Leu Cys Ala Gly Ala Leu Val Leu Ala Gly
                20                  25                  30

Gly Phe Phe Leu Leu Gly Phe Leu Phe Gly Trp Phe Ile Lys Ser
                35                  40                  45

Ser Asn Glu Ala Thr Asn Ile Thr Pro Lys His Asn Met Lys Ala
                50                  55                  60

Phe Leu Asp Glu Leu Lys Ala Glu Asn Ile Lys Lys Phe Leu Tyr
                65                  70                  75

Asn Phe Thr Gln Ile Pro His Leu Ala Gly Thr Glu Gln Asn Phe
                80                  85                  90

Gln Leu Ala Lys Gln Ile Gln Ser Gln Trp Lys Glu Phe Gly Leu
                95                 100                 105

Asp Ser Val Glu Leu Ala His Tyr Asp Val Leu Leu Ser Tyr Pro
               110                 115                 120

Asn Lys Thr His Pro Asn Tyr Ile Ser Ile Ile Asn Glu Asp Gly
               125                 130                 135

Asn Glu Ile Phe Asn Thr Ser Leu Phe Glu Pro Pro Pro Pro Gly
               140                 145                 150

Tyr Glu Asn Val Ser Asp Ile Val Pro Pro Phe Ser Ala Phe Ser
               155                 160                 165

Pro Gln Gly Met Pro Glu Gly Asp Leu Val Tyr Val Asn Tyr Ala
               170                 175                 180

Arg Thr Glu Asp Phe Phe Lys Leu Glu Arg Asp Met Lys Ile Asn
               185                 190                 195

Cys Ser Gly Lys Ile Val Ile Ala Arg Tyr Gly Lys Val Phe Arg
               200                 205                 210

Gly Asn Lys Val Lys Asn Ala Gln Leu Ala Gly Ala Lys Gly Val
               215                 220                 225

Ile Leu Tyr Ser Asp Pro Ala Asp Tyr Phe Ala Pro Gly Val Lys
               230                 235                 240

Ser Tyr Pro Asp Gly Trp Asn Leu Pro Gly Gly Gly Val Gln Arg
               245                 250                 255

Gly Asn Ile Leu Asn Leu Asn Gly Ala Gly Asp Pro Leu Thr Pro
               260                 265                 270

Gly Tyr Pro Ala Asn Glu Tyr Ala Tyr Arg Arg Gly Ile Ala Glu
               275                 280                 285

Ala Val Gly Leu Pro Ser Ile Pro Val His Pro Ile Gly Tyr Tyr
               290                 295                 300
```

-continued

```
Asp Ala Gln Lys Leu Leu Glu Lys Met Gly Gly Ser Ala Pro Pro
            305                 310                 315
Asp Ser Ser Trp Arg Gly Ser Leu Lys Val Pro Tyr Asn Val Gly
            320                 325                 330
Pro Gly Phe Thr Gly Asn Phe Ser Thr Gln Lys Val Lys Met His
            335                 340                 345
Ile His Ser Thr Asn Glu Val Thr Arg Ile Tyr Asn Val Ile Gly
            350                 355                 360
Thr Leu Arg Gly Ala Val Glu Pro Asp Arg Tyr Val Ile Leu Gly
            365                 370                 375
Gly His Arg Asp Ser Trp Val Phe Gly Gly Ile Asp Pro Gln Ser
            380                 385                 390
Gly Ala Ala Val Val His Glu Ile Val Arg Ser Phe Gly Thr Leu
            395                 400                 405
Lys Lys Glu Gly Trp Arg Pro Arg Arg Thr Ile Leu Phe Ala Ser
            410                 415                 420
Trp Asp Ala Glu Glu Phe Gly Leu Leu Gly Ser Thr Glu Trp Ala
            425                 430                 435
Glu Glu Asn Ser Arg Leu Leu Gln Glu Arg Gly Val Ala Tyr Ile
            440                 445                 450
Asn Ala Asp Ser Ser Ile Glu Gly Asn Tyr Thr Leu Arg Val Asp
            455                 460                 465
Cys Thr Pro Leu Met Tyr Ser Leu Val His Asn Leu Thr Lys Glu
            470                 475                 480
Leu Lys Ser Pro Asp Glu Gly Phe Glu Gly Lys Ser Leu Tyr Glu
            485                 490                 495
Ser Trp Thr Lys Lys Ser Pro Ser Pro Glu Phe Ser Gly Met Pro
            500                 505                 510
Arg Ile Ser Lys Leu Gly Ser Gly Asn Asp Phe Glu Val Phe Phe
            515                 520                 525
Gln Arg Leu Gly Ile Ala Ser Gly Arg Ala Arg Tyr Thr Lys Asn
            530                 535                 540
Trp Glu Thr Asn Lys Phe Ser Gly Tyr Pro Leu Tyr His Ser Val
            545                 550                 555
Tyr Glu Thr Tyr Glu Leu Val Glu Lys Phe Tyr Asp Pro Met Phe
            560                 565                 570
Lys Tyr His Leu Thr Val Ala Gln Val Arg Gly Gly Met Val Phe
            575                 580                 585
Glu Leu Ala Asn Ser Ile Val Leu Pro Phe Asp Cys Arg Asp Tyr
            590                 595                 600
Ala Val Val Leu Arg Lys Tyr Ala Asp Lys Ile Tyr Ser Ile Ser
            605                 610                 615
Met Lys His Pro Gln Glu Met Lys Thr Tyr Ser Val Ser Phe Asp
            620                 625                 630
Ser Leu Phe Ser Ala Val Lys Asn Phe Thr Glu Ile Ala Ser Lys
            635                 640                 645
Phe Ser Glu Arg Leu Gln Asp Phe Asp Lys Ser Asn Pro Ile Val
            650                 655                 660
Leu Arg Met Met Asn Asp Gln Leu Met Phe Leu Glu Arg Ala Phe
            665                 670                 675
Ile Asp Pro Leu Gly Leu Pro Asp Arg Pro Phe Tyr Arg His Val
            680                 685                 690
Ile Tyr Ala Pro Ser Ser His Asn Lys Tyr Ala Gly Glu Ser Phe
```

```
                        695                 700                 705
Pro Gly Ile Tyr Asp Ala Leu Phe Asp Ile Glu Ser Lys Val Asp
                710                 715                 720

Pro Ser Lys Ala Trp Gly Glu Val Lys Arg Gln Ile Tyr Val Ala
                725                 730                 735

Ala Phe Thr Val Gln Ala Ala Ala Glu Thr Leu Ser Glu Val Ala
                740                 745                 750

<210> SEQ ID NO 5
<211> LENGTH: 28
<212> TYPE: DNA
<213> ORGANISM: Artificial sequence
<220> FEATURE:
<221> NAME/KEY: primer_bind
<223> OTHER INFORMATION: sense primer designed for only amplifying
      the first intron of the PSMA-like gene on chromosome 11q

<400> SEQUENCE: 5
gccttcattt tcagaacatc tcatgcat                                        28

<210> SEQ ID NO 6
<211> LENGTH: 25
<212> TYPE: DNA
<213> ORGANISM: Artificial sequence
<220> FEATURE:
<221> NAME/KEY: primer_bind
<223> OTHER INFORMATION: antisense primer designed for only amplifying
      the first intron of the PSMA-like gene on chromosome 11q

<400> SEQUENCE: 6
gtccatataa actttcaaga atgtg                                           25

<210> SEQ ID NO 7
<211> LENGTH: 20
<212> TYPE: DNA
<213> ORGANISM: Artificial sequence
<220> FEATURE:
<221> NAME/KEY: primer_bind
<223> OTHER INFORMATION: sense oligonucleotide primer based upon
      intronic sequences of the PSMA genomic clone used to amplify the
      corresponding regions of the PSMA-like gene (exon 2)

<400> SEQUENCE: 7
ctcacctaat gtcagaggta                                                 20

<210> SEQ ID NO 8
<211> LENGTH: 20
<212> TYPE: DNA
<213> ORGANISM: Artificial sequence
<220> FEATURE:
<221> NAME/KEY: primer_bind
<223> OTHER INFORMATION: antisense oligonucleotide primer based upon
      intronic sequences of the PSMA genomic clone used to amplify the
      corresponding regions of the PSMA-like gene (exon 2)

<400> SEQUENCE: 8
agtatagtcc tcctcagatg                                                 20

<210> SEQ ID NO 9
<211> LENGTH: 24
<212> TYPE: DNA
<213> ORGANISM: Artificial sequence
<220> FEATURE:
<221> NAME/KEY: primer_bind
<223> OTHER INFORMATION: sense oligonucleotide primer based upon
      intronic sequences of the PSMA genomic clone used to amplify
      the corresponding regions of the PSMA-like gene (exon 3)
```

```
<400> SEQUENCE: 9
caaagtactt ttgtgtaact ctgc                                              24

<210> SEQ ID NO 10
<211> LENGTH: 22
<212> TYPE: DNA
<213> ORGANISM: Artificial sequence
<220> FEATURE:
<221> NAME/KEY: primer_bind
<223> OTHER INFORMATION: antisense oligonucleotide primer based upon
      intronic sequences of the PSMA genomic clone used to amplify the
      corresponding regions of the PSMA-like gene (exon 3)

<400> SEQUENCE: 10
cataggaaag tagttgacac gg                                                22

<210> SEQ ID NO 11
<211> LENGTH: 22
<212> TYPE: DNA
<213> ORGANISM: Artificial sequence
<220> FEATURE:
<221> NAME/KEY: primer_bind
<223> OTHER INFORMATION: sense oligonucleotide primer based upon
      intronic sequences of the PSMA genomic clone used to amplify
      the corresponding regions of the PSMA-like gene (exon 4)

<400> SEQUENCE: 11
cctgaaggat tcattcaccc tc                                                22

<210> SEQ ID NO 12
<211> LENGTH: 24
<212> TYPE: DNA
<213> ORGANISM: Artificial sequence
<220> FEATURE:
<221> NAME/KEY: primer_bind
<223> OTHER INFORMATION: antisense oligonucleotide primer based upon
      intronic sequences of the PSMA genomic clone used to amplify the
      corresponding regions of the PSMA-like gene (exon 4)

<400> SEQUENCE: 12
gaccctttaa ttatcggctg aaca                                              24

<210> SEQ ID NO 13
<211> LENGTH: 22
<212> TYPE: DNA
<213> ORGANISM: Artificial sequence
<220> FEATURE:
<221> NAME/KEY: primer_bind
<223> OTHER INFORMATION: sense oligonucleotide primer based upon
      intronic sequences of the PSMA genomic clone used to amplify the
      corresponding regions of the PSMA-like gene (exons 5-6)

<400> SEQUENCE: 13
atgtccaaca gtccccatgc ag                                                22

<210> SEQ ID NO 14
<211> LENGTH: 22
<212> TYPE: DNA
<213> ORGANISM: Artificial sequence
<220> FEATURE:
<221> NAME/KEY: primer_bind
<223> OTHER INFORMATION: antisense oligonucleotide primer based upon
      intronic sequences of the PSMA genomic clone used to amplify the
      corresponding regions of the PSMA-like gene (exons 5-6)

<400> SEQUENCE: 14
gacatgctta gtccattgta cc                                                22
```

```
<210> SEQ ID NO 15
<211> LENGTH: 22
<212> TYPE: DNA
<213> ORGANISM: Artificial sequence
<220> FEATURE:
<221> NAME/KEY: primer_bind
<223> OTHER INFORMATION: sense oligonucleotide primer based upon
      intronic sequences of the PSMA genomic clone used to amplify the
      corresponding regions of the PSMA-like gene (exon 7)

<400> SEQUENCE: 15
gaaccgtttg aatgaaactg ag                                              22

<210> SEQ ID NO 16
<211> LENGTH: 22
<212> TYPE: DNA
<213> ORGANISM: Artificial sequence
<220> FEATURE:
<221> NAME/KEY: primer_bind
<223> OTHER INFORMATION: antisense oligonucleotide primer based upon
      intronic sequences of the PSMA genomic clone used to amplify the
      corresponding regions of the PSMA-like gene (exon 7)

<400> SEQUENCE: 16
ttacccaaat agccatccat gg                                              22

<210> SEQ ID NO 17
<211> LENGTH: 23
<212> TYPE: DNA
<213> ORGANISM: Artificial sequence
<220> FEATURE:
<221> NAME/KEY: primer_bind
<223> OTHER INFORMATION: sense oligonucleotide primer based upon
      intronic sequences of the PSMA genomic clone used to amplify the
      corresponding regions of the PSMA-like gene (exons 8-9)

<400> SEQUENCE: 17
gcagatgctc aataagtgaa tcc                                             23

<210> SEQ ID NO 18
<211> LENGTH: 24
<212> TYPE: DNA
<213> ORGANISM: Artificial sequence
<220> FEATURE:
<221> NAME/KEY: primer_bind
<223> OTHER INFORMATION: antisense oligonucleotide primer based upon
      intronic sequences of the PSMA genomic clone used to amplify the
      corresponding regions of the PSMA-like gene (exons 8-9)

<400> SEQUENCE: 18
ccagcacata acagttactt gatc                                            24

<210> SEQ ID NO 19
<211> LENGTH: 22
<212> TYPE: DNA
<213> ORGANISM: Artificial sequence
<220> FEATURE:
<221> NAME/KEY: primer_bind
<223> OTHER INFORMATION: sense oligonucleotide primer based upon
      intronic sequences of the PSMA genomic clone used to amplify the
      corresponding regions of the PSMA-like gene (exon 10)

<400> SEQUENCE: 19
tagatgctat tgagtcgttt gc                                              22

<210> SEQ ID NO 20
<211> LENGTH: 22
```

```
<212> TYPE: DNA
<213> ORGANISM: Artificial sequence
<220> FEATURE:
<221> NAME/KEY: primer_bind
<223> OTHER INFORMATION: antisense oligonucleotide primer based upon
      intronic sequences of the PSMA genomic clone used to amplify the
      corresponding regions of the PSMA-like gene (exon 10)

<400> SEQUENCE: 20
aaactgagac tcagataggc tg                                              22

<210> SEQ ID NO 21
<211> LENGTH: 22
<212> TYPE: DNA
<213> ORGANISM: Artificial sequence
<220> FEATURE:
<221> NAME/KEY: primer_bind
<223> OTHER INFORMATION: sense oligonucleotide primer based upon
      intronic sequences of the PSMA genomic clone used to amplify the
      corresponding regions of the PSMA-like gene (exon 11)

<400> SEQUENCE: 21
ctgggcttgg tagtgtcctg gg                                              22

<210> SEQ ID NO 22
<211> LENGTH: 24
<212> TYPE: DNA
<213> ORGANISM: Artificial sequence
<220> FEATURE:
<221> NAME/KEY: primer_bind
<223> OTHER INFORMATION: antisense oligonucleotide primer based upon
      intronic sequences of the PSMA genomic clone used to amplify the
      corresponding regions of the PSMA-like gene (exon 11)

<400> SEQUENCE: 22
gcttggcaaa caagtcctgg ctac                                            24

<210> SEQ ID NO 23
<211> LENGTH: 22
<212> TYPE: DNA
<213> ORGANISM: Artificial sequence
<220> FEATURE:
<221> NAME/KEY: primer_bind
<223> OTHER INFORMATION: sense oligonucleotide primer based upon
      intronic sequences of the PSMA genomic clone used to amplify the
      corresponding regions of the PSMA-like gene (exon 12)

<400> SEQUENCE: 23
tgtcgttaat atgggtcagc tc                                              22

<210> SEQ ID NO 24
<211> LENGTH: 22
<212> TYPE: DNA
<213> ORGANISM: Artificial sequence
<220> FEATURE:
<221> NAME/KEY: primer_bind
<223> OTHER INFORMATION: antisense oligonucleotide primer based upon
      intronic sequences of the PSMA genomic clone used to amplify the
      corresponding regions of the PSMA-like gene (exon 12)

<400> SEQUENCE: 24
ttaactagac tgctgctcct ag                                              22

<210> SEQ ID NO 25
<211> LENGTH: 22
<212> TYPE: DNA
<213> ORGANISM: Artificial sequence
<220> FEATURE:
<221> NAME/KEY: primer_bind
```

```
<223> OTHER INFORMATION: sense oligonucleotide primer based upon
      intronic sequences of the PSMA genomic clone used to amplify the
      corresponding regions of the PSMA-like gene (exon 13)

<400> SEQUENCE: 25
tggtaggaat ttagcagtgg tc                                          22

<210> SEQ ID NO 26
<211> LENGTH: 22
<212> TYPE: DNA
<213> ORGANISM: Artificial sequence
<220> FEATURE:
<221> NAME/KEY: primer_bind
<223> OTHER INFORMATION: antisense oligonucleotide primer based upon
      intronic sequences of the PSMA genomic clone used to amplify the
      corresponding regions of the PSMA-like gene (exon 13)

<400> SEQUENCE: 26
gatgctacta atgggctacc tc                                          22

<210> SEQ ID NO 27
<211> LENGTH: 22
<212> TYPE: DNA
<213> ORGANISM: Artificial sequence
<220> FEATURE:
<221> NAME/KEY: primer_bind
<223> OTHER INFORMATION: sense oligonucleotide primer based upon
      intronic sequences of the PSMA genomic clone used to amplify the
      corresponding regions of the PSMA-like gene (exon 14)

<400> SEQUENCE: 27
cttctggtta atggacatct ag                                          22

<210> SEQ ID NO 28
<211> LENGTH: 22
<212> TYPE: DNA
<213> ORGANISM: Artificial sequence
<220> FEATURE:
<221> NAME/KEY: primer_bind
<223> OTHER INFORMATION: antisense oligonucleotide primer based upon
      intronic sequences of the PSMA genomic clone used to amplify the
      corresponding regions of the PSMA-like gene (exon 14)

<400> SEQUENCE: 28
caatcccaca ctgaattcag tg                                          22

<210> SEQ ID NO 29
<211> LENGTH: 22
<212> TYPE: DNA
<213> ORGANISM: Artificial sequence
<220> FEATURE:
<221> NAME/KEY: primer_bind
<223> OTHER INFORMATION: sense oligonucleotide primer based upon
      intronic sequences of the PSMA genomic clone used to amplify the
      corresponding regions of the PSMA-like gene (exon 15)

<400> SEQUENCE: 29
agaatggggt ttagtttaat gg                                          22

<210> SEQ ID NO 30
<211> LENGTH: 21
<212> TYPE: DNA
<213> ORGANISM: Artificial sequence
<220> FEATURE:
<221> NAME/KEY: primer_bind
<223> OTHER INFORMATION: antisense oligonucleotide primer based upon
      intronic sequences of the PSMA genomic clone used to amplify the
      corresponding regions of the PSMA-like gene (exon 15)
```

-continued

```
<400> SEQUENCE: 30
tgagtcactt tttggagtca g                                              21

<210> SEQ ID NO 31
<211> LENGTH: 22
<212> TYPE: DNA
<213> ORGANISM: Artificial sequence
<220> FEATURE:
<221> NAME/KEY: primer_bind
<223> OTHER INFORMATION: sense oligonucleotide primer based upon
      intronic sequences of the PSMA genomic clone used to amplify the
      corresponding regions of the PSMA-like gene (exons 16-17)

<400> SEQUENCE: 31
ttgtaagcta tccctataag ag                                             22

<210> SEQ ID NO 32
<211> LENGTH: 22
<212> TYPE: DNA
<213> ORGANISM: Artificial sequence
<220> FEATURE:
<221> NAME/KEY: primer_bind
<223> OTHER INFORMATION: antisense oligonucleotide primer based upon
      intronic sequences of the PSMA genomic clone used to amplify the
      corresponding regions of the PSMA-like gene (exons 16-17)

<400> SEQUENCE: 32
agttcagcaa cagtcatgtt ag                                             22

<210> SEQ ID NO 33
<211> LENGTH: 22
<212> TYPE: DNA
<213> ORGANISM: Artificial sequence
<220> FEATURE:
<221> NAME/KEY: primer_bind
<223> OTHER INFORMATION: sense oligonucleotide primer based upon
      intronic sequences of the PSMA genomic clone used to amplify the
      corresponding regions of the PSMA-like gene (exon 18)

<400> SEQUENCE: 33
gggtggtcct gaaaccaatc cc                                             22

<210> SEQ ID NO 34
<211> LENGTH: 21
<212> TYPE: DNA
<213> ORGANISM: Artificial sequence
<220> FEATURE:
<221> NAME/KEY: primer_bind
<223> OTHER INFORMATION: antisense oligonucleotide primer based upon
      intronic sequences of the PSMA genomic clone used to amplify the
      corresponding regions of the PSMA-like gene (exon 18)

<400> SEQUENCE: 34
gtgatattac agaaaggagt c                                              21

<210> SEQ ID NO 35
<211> LENGTH: 22
<212> TYPE: DNA
<213> ORGANISM: Artificial sequence
<220> FEATURE:
<221> NAME/KEY: primer_bind
<223> OTHER INFORMATION: sense oligonucleotide primer based upon
      intronic sequences of the PSMA genomic clone used to amplify the
      corresponding regions of the PSMA-like gene (exon 19)

<400> SEQUENCE: 35
atccaggaat tgcagagtgc tc                                             22
```

```
<210> SEQ ID NO 36
<211> LENGTH: 22
<212> TYPE: DNA
<213> ORGANISM: Artificial sequence
<220> FEATURE:
<221> NAME/KEY: primer_bind
<223> OTHER INFORMATION: antisense oligonucleotide primer based upon
      intronic sequences of the PSMA genomic clone used to amplify the
      corresponding regions of the PSMA-like gene (exon 19)

<400> SEQUENCE: 36
ttcagtttta atccataggg ag                                              22

<210> SEQ ID NO 37
<211> LENGTH: 24
<212> TYPE: DNA
<213> ORGANISM: Artificial sequence
<220> FEATURE:
<221> NAME/KEY: primer_bind
<223> OTHER INFORMATION: sense primer (exon 10) used for performing
      PCR on cDNAs from various tissues

<400> SEQUENCE: 37
acagatatgt cattctggga ggtc                                            24

<210> SEQ ID NO 38
<211> LENGTH: 24
<212> TYPE: DNA
<213> ORGANISM: Artificial sequence
<220> FEATURE:
<221> NAME/KEY: primer_bind
<223> OTHER INFORMATION: antisense primer (exon 16) used for
      performing PCR on cDNAs from various
      tissues

<400> SEQUENCE: 38
actgtgatac agtggatagc cgct                                            24
```